United States Patent [19]

Masumoto et al.

[11] Patent Number: 5,648,533
[45] Date of Patent: Jul. 15, 1997

[54] PROCESS OF PRODUCING 2-IMINOTHIAZOLINE DERIVATIVES AND PROCESS OF PRODUCING THEIR INTERMEDIATES

[75] Inventors: Katuhisa Masumoto, Ibaraki; Toshio Nagatomi, Takarazuka; Akihiko Nakamura, Nishinomiya; Yoshimi Yamada, Toyono-gun, all of Japan

[73] Assignee: Sumitomo Chemical Co., Ltd., Osaka-fu, Japan

[21] Appl. No.: 434,589

[22] Filed: May 4, 1995

Related U.S. Application Data

[62] Division of Ser. No. 160,261, Dec. 2, 1993, Pat. No. 5,463,069.

[30] Foreign Application Priority Data

Dec. 4, 1992 [JP] Japan .................................. 4-325259
Feb. 5, 1993 [JP] Japan .................................. 5-018609

[51] Int. Cl.$^6$ ................................................ C07C 335/16
[52] U.S. Cl. .................................................. 564/20
[58] Field of Search .................................................. 564/29

[56] References Cited

U.S. PATENT DOCUMENTS

| | | | |
|---|---|---|---|
| 3,546,344 | 12/1970 | Martin et al. | 564/29 X |
| 4,665,083 | 5/1987 | Lempert et al. | 564/29 X |
| 5,244,863 | 9/1993 | Kawamura et al. | 564/29 X |

FOREIGN PATENT DOCUMENTS

| | | |
|---|---|---|
| 529482A1 | 3/1993 | European Pat. Off. . |
| 529481A1 | 3/1993 | European Pat. Off. . |
| 1511325 | 12/1967 | France . |
| 53-90222 | 8/1978 | Japan . |

OTHER PUBLICATIONS

Johnson et al., *J. Org. Chem.*, Jan. 1964, vol. 29, pp. 153–157.

Bramley et al., *J. Chem. Soc. Perkin Trans. I*, 1987, pp. 639–643.

Sugiyama et al., *Chem. Pharm. Bull.*, 37(8), 1989, pp. 2122–2131.

*Primary Examiner*—Robert Gerstl
*Attorney, Agent, or Firm*—Birch, Stewart, Kolasch & Birch, LLP

[57] ABSTRACT

There is disclosed a process of producing a 2-iminothiazoline derivative of the general formula [II], characterized in that a thiourea derivative of the general formula [I] is treated with an acid. Also disclosed are a process of producing an N-substituted N-arylcyanamide derivative of the general formula [VI], characterized in that an N-arylcyanamide derivative of the general formula [IV] is reacted with an allyl halide derivative of the general formula [V] in an aprotic polar solvent in the presence of an iodide and an alkali metal carbonate; and a process of producing an N-substituted N-arylthiourea derivative of the general formula [VII], characterized in that an N-substituted N-arylcyanamide derivative of the general formula [VI] obtained as described above is further reacted with a chemical species which generates sulfide ion or hydrogensulfide ion.

5 Claims, No Drawings

PROCESS OF PRODUCING 2-IMINOTHIAZOLINE DERIVATIVES AND PROCESS OF PRODUCING THEIR INTERMEDIATES

This application is a divisional of application Ser. No. 08/160,261, filed on Dec. 2, 1993 U.S. Pat. No. 5,463,064, the entire contents of which are hereby incorporated by reference.

The present invention relates to a process of producing 2-iminothiazoline derivatives that are useful as intermediates for the production of medicaments and agricultural chemicals, particularly as intermediates for the production of herbicidal compounds (see, e.g., U.S. Pat. No. 5,244,863 and European Patent Publication No. 0529482A). The present invention also relates to a process of producing some intermediates for the production of these 2-iminothiazoline derivatives.

As a conventional process of producing 2-iminothiazoline derivatives, for example, there is a process of the following scheme as described in J. Chem. Soc. Perkin Trans. I, 3, 639 (1987):

<Scheme 1>

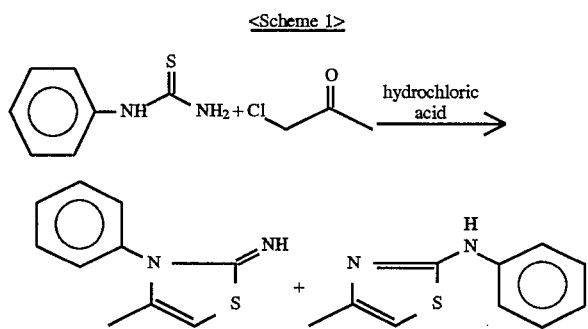

This process has a disadvantage of having poor regioselectivity in the reaction as depicted in the above scheme and can only find particularly applications; therefore, it is not always satisfactory as a process of producing 2-iminothiazoline derivatives.

The present inventors have intensively studied a production process for 2-iminothiazoline derivatives of the general formula [II] as depicted below, and found that such 2-iminothiazoline derivatives can be obtained by acid treatment of thiourea derivatives of the general formula [I] as depicted below, thereby completing the present invention.

Thus, the present invention provides a process of producing a 2-iminothiazoline derivative of the general formula:

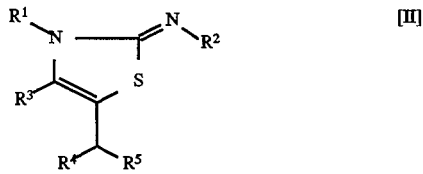

[II]

wherein $R^1$ is optionally substituted alkyl, optionally substituted cycloalkyl, optionally substituted aryl or optionally substituted heteroaryl; $R^2$ is hydrogen, optionally substituted alkyl, optionally substituted cycloalkyl, optionally substituted aryl, optionally substituted alkylcarbonyl, optionally substituted cycloalkylcarbonyl, optionally substituted arylcarbonyl, optionally substituted alkoxycarbonyl, optionally substituted cycloalkyloxycarbonyl or optionally substituted aryloxycarbonyl; and $R^3$, $R^4$ and $R^5$ are the same or different, each of which is hydrogen, optionally substituted alkyl or optionally substituted aryl, the process comprising the step of treating a thiourea derivative of the general formula:

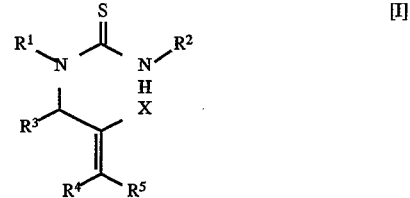

[I]

wherein $R^1$, $R^2$, $R^3$, $R^4$ and $R^5$ are each as defined above and X is halogen, with an acid.

Also provided is a process of producing an N-substituted N-arylcyanamide derivative of the general formula:

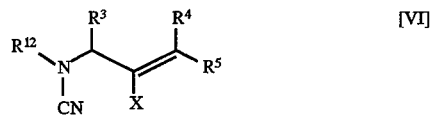

[VI]

wherein $R^3$, $R^4$, $R^5$ and X are each as defined above and $R^{12}$ is optionally substituted aryl, the process comprising the step of reacting an N-arylcyanamide derivative of the general formula:

[IV]

wherein $R^{12}$ is as defined above, with an allyl halide derivative of the general formula:

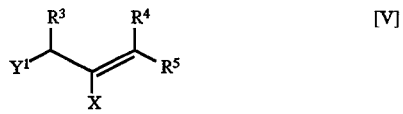

[V]

wherein $R^3$, $R^4$, $R^5$ and X are each as defined above and $Y^1$ is chlorine or bromine, in an aprotic polar solvent in the presence of an iodide and an alkali metal carbonate.

Further provided is a process of producing an N-substituted N-arylthiourea derivative of the general formula:

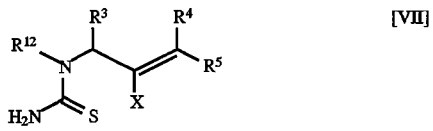

[VII]

wherein $R^3$, $R^4$, $R^5$, $R^{12}$ and X are each as defined above, the process comprising the step of reacting an N-substituted N-arylcyanamide derivative of the general formula:

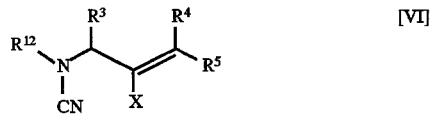

[VI]

wherein $R^3$, $R^4$, $R^5$, $R^{12}$ and X are each as defined above, with a chemical species which generates sulfide ion or hydrogensulfide ion.

The process of producing a 2-iminothiazoline derivative according to the present invention is characterized in that a particular thiourea derivative is subjected to acid treatment.

In the present invention, typical examples of the $R^1$ are $C_{1-8}$ alkyl optionally substituted with at least one substituent (e.g., $C_{1-8}$ alkoxy, aryl, $C_{3-8}$ cycloalkyl, etc.); $C_{3-8}$ cycloalkyl optionally substituted with at least one substituent (e.g., $C_{1-8}$ alkyl, $C_{1-8}$ alkoxy, aryl, etc.); aryl optionally substituted with at least one substituent (e.g., $C_{1-8}$ alkyl optionally substituted with at least one halogen atom; $C_{1-8}$ alkoxy optionally substituted with at least one halogen atom; aryl, nitro, halogen, etc.); and heteroaryl optionally substituted with at least one substituent (e.g., $C_{1-8}$ alkyl optionally substituted with at least one halogen atom; $C_{1-8}$ alkoxy optionally substituted with at least one halogen atom; aryl, nitro, halogen, etc.).

Typical examples of the $R^2$ are hydrogen, $C_{1-8}$ alkyl optionally substituted with at least one substituent (e.g., $C_{1-8}$ alkoxy, aryl, $C_{3-8}$ cycloalkyl, etc.); $C_{3-8}$ cycloalkyl optionally substituted with at least one substituent (e.g., $C_{1-8}$ alkyl, $C_{1-8}$ alkoxy, aryl, etc.); aryl optionally substituted with at least one substituent (e.g., $C_{1-8}$ alkyl, $C_{1-8}$ alkoxy, aryl, nitro, halogen, etc.); alkyl ($C_{1-8}$) carbonyl optionally substituted with at least one substituent (e.g., $C_{1-8}$ alkoxy, aryl, $C_{3-8}$ cycloalkyl, etc.); cycloalkyl ($C_{3-8}$) carbonyl optionally substituted with at least one substituent (e.g., $C_{1-8}$ alkyl, $C_{1-8}$ alkoxy, aryl, etc.); arylcarbonyl optionally substituted with at least one substituent (e.g., $C_{1-8}$ alkyl, $C_{1-8}$ alkoxy, aryl, nitro, halogen, etc.); alkoxy ($C_{1-8}$) carbonyl optionally substituted at least one substituent (e.g., $C_{1-8}$ alkoxy, aryl, $C_{3-8}$ cycloalkyl, etc.); cycloalkyl ($C_{3-8}$) oxycarbonyl optionally substituted with at least one substituent (e.g., $C_{1-8}$ alkyl, $C_{1-8}$ alkoxy, aryl, etc.); and aryloxycarbonyl optionally substituted with at least one substituent (e.g., $C_{1-8}$ alkyl optionally substituted with at least one halogen atom; $C_{1-8}$ alkoxy optionally substituted with at least one halogen atom; aryl, nitro, halogen, etc.).

Typical examples of each of the $R^3$, $R^4$ and $R^5$ are hydrogen, $C_{1-8}$ alkyl optionally substituted with at least one substituent (e.g., $C_{1-8}$ alkoxy, aryl, $C_{3-8}$ cycloalkyl, etc.); and aryl optionally substituted with at least one substituent (e.g., $C_{1-8}$ alkyl, $C_{1-8}$ alkoxy, aryl, nitro, halogen, etc.).

In the above examples, the term "alkyl" means a member of alkyl groups such as methyl, ethyl, propyl, isopropyl, butyl, isobutyl, sec-butyl, tert-butyl, hexyl and octyl; the term "cycloalkyl" means a member of cycloalkyl groups such as cyclopropyl, cyclobutyl, cyclopentyl, cyclohexyl and cyclooctyl; the term "alkoxy" means a member of alkoxy groups such as methoxy, ethoxy, propyloxy, isopropyloxy, butoxy, isobutyloxy, sec-butyloxy, tert-butyloxy, hexyloxy and octyloxy; the term "aryl" means a member of aryl groups such as phenyl, α-naphthyl and β-naphthyl; the term "heteroaryl" means a member of heteroaryl groups such as pyridyl, pyrimidinyl, thienyl, imidazolyl, thiazolyl and oxazolyl; and the term "halogen" means a member of halogen atoms such as chlorine, bromine, iodine and fluorine. As also used therein, the term "optionally substituted with at least one substituent" or "optionally substituted with at least one halogen atom" means that at least one (e.g., one to three) hydrogen atoms on each group may be optionally replaced by the same or different substituents or halogen atoms, respectively. As the X, chlorine or bromine is usually used.

Specific examples of the thiourea derivative of the general formula [I] used as a starting material in the present invention are as follows:

N-(3-(trifluoromethyl)phenyl)-N-(2-chloro-2-propenyl) thiourea;
N-(3,5-dichlorophenyl)-N-(2-chloro-2-propenyl)thiourea;
N-(4-methoxyphenyl)-N-(2-chloro-2-propenyl)thiourea;
N-(3-chlorophenyl)-N-(2-chloro-2-propenyl)thiourea;
N-(3-(trifluoromethoxy)phenyl)-N-(2-chloro-2-propenyl) thiourea;
N-(4-fluoro-3-(trifluoromethyl)phenyl)-N-(2-chloro-2-propenyl)thiourea;
N-butyl-N-(2-chloro-2-propenyl)-N'-phenylthiourea;
N-(3-(trifluoromethyl)phenyl)-N-(2-chloro-1-methyl-2-propenyl)thiourea;
N-(2-chlorophenyl)-N-(2-chloro-2-propenyl)thiourea;
N-(3-(trifluoromethyl)phenyl)-N-(2-bromo-2-propenyl) thiourea;
N-butyl-N-(2-chloro-2-propenyl)-N'-butylthiourea;
N-butyl-N-(2-chloro-2-propenyl)-N'-benzylthiourea;
N-(3-(trifluoromethyl)phenyl)-N-(2-chloro-2-butenyl) thiourea;
N-(3-(trifluoromethoxy)phenyl)-N-(2-chloro-2-butenyl) thiourea; and
N-(4-fluoro-3-(trifluoromethoxy)phenyl)-N-(2-chloro-2-butenyl)thiourea.

Specific examples of the 2-iminothiazoline derivative of the general formula [II] are as follows:
2-imino-3-(3-(trifluoromethyl)phenyl)-5-methyl-4-thiazoline;
2-imino-3-(3,5-dichlorophenyl)-5-methyl-4-thiazoline;
2-imino-3-(4-methoxyphenyl)-5-methyl-4-thiazoline;
2-imino-3-(3-chlorophenyl)-5-methyl-4-thiazoline;
2-imino-3-(3-(trifluoromethoxy)phenyl)-5-methyl-4-thiazoline;
2-imino-3-(4-fluoro-3-(trifluoromethyl)phenyl)-5-methyl-4-thiazoline;
2-(N-phenylimino)-3-butyl-5-methyl-4-thiazoline;
2-imino-3-(3-(trifluoromethyl)phenyl)-4,5-dimethyl-4-thiazoline;
2-imino-3-(2-chlorophenyl)-5-methyl-4-thiazoline;
2-(N-butylimino)-3-butyl-5-methyl-4-thiazoline;
2-(N-benzylimino)-3-butyl-5-methyl-4-thiazoline;
2-imino-3-(3-(trifluoromethyl)phenyl)-5-ethyl-4-thiazoline;
2-imino-3-(3-(trifluoromethoxy)phenyl)-5-ethyl-4-thiazoline; and
2-imino-3-(4-fluoro-3-(trifluoromethyl)phenyl)-5-ethyl-4-thiazoline.

As the acid used in the present invention, there can be mentioned protonic acids, metal salts having Lewis acidity, and mixtures thereof.

In one embodiment of the acid treatment according to the present invention, a 2-iminothiazoline derivative of the general formula [II] can be obtained by treatment of a thiourea derivative of the general formula [I] with a protonic acid having strong acidity.

Typical examples of the protonic acid having strong acidity are sulfuric acid (usually having a concentration of 100% to 50%, preferably 100% to 75%); inorganic acids having acidity which is equal to or stronger than that of sulfuric acid; and organic acids having strong acidity, such as trifluoromethanesulfonic acid, methanesulfonic acid and trifluoroacetic acid.

The reaction is usually carried out without any solvent, but an inert solvent against the acid may be used. Examples of the solvent which can be used in the reaction are aliphatic hydrocarbon solvents such as heptane and hexane; aromatic hydrocarbon solvents such as benzene, toluene and xylene; halogenated hydrocarbon solvents such as monochlorobenzene, chloroform and ethylene dichloride; carboxylic acid solvents such as formic acid and acetic acid; and mixtures thereof. The reaction is usually carried out at a temperature of 0° to 150° C., preferably 20° to 120° C., for 0.2 to 24 hours. The protonic acid having strong acidity is usually used at a proportion of 1 to 1000 moles to one mole of the thiourea derivative of the general formula [I].

After completion of the reaction, water is added to the reaction mixture, which is then neutralized by addition of an alkali, and the neutralized mixture is subjected to an ordinary post-treatment such as extraction with an organic solvent and concentration, and if necessary, any purification such as chromatography may be further utilized to give the desired 2-iminothiazoline derivative of the general formula [II].

In another embodiment of the acid treatment according to the present invention, a 2-iminothiazoline derivative of the general formula [II] can be obtained by treatment of a thiourea derivative of the general formula [I] with a metal salt having Lewis acidity, and if necessary, a protonic acid.

Typical examples of the metal salt having Lewis acidity are stannic halides such as stannic chloride ($SnCl_4$), stannic bromide ($SnBr_4$) and stannic iodide ($SnI_4$); zinc halides such as zinc chloride ($ZnCl_2$), zinc bromide ($ZnBr_2$) and zinc iodide ($ZnI_2$); cupric halides such as cupric chloride ($CuCl_2$); and aluminum halides such as aluminum chloride ($AlCl_3$). These metal salts are not always required to be in anhydrous form, and they may contain crystal water.

Typical examples of the protonic acid are inorganic acids such as hydrochloric acid and sulfuric acid; and organic acids such as methanesulfonic acid, trifluoroacetic acid and trifluoromethanesulfonic acid. The addition of such a protonic acid is not always required when the metal salt having Lewis acidity is solvolized in the reaction system to form a protonic acid.

The reaction is usually carried out in a solvent. Typical examples of the solvent which can be used in the reaction are aliphatic hydrocarbon solvents such as heptane and hexane; aromatic hydrocarbon solvents such as benzene, toluene and xylene; halogenated hydrocarbon solvents such as monochlorobenzene, chloroform and ethylene dichloride; ether solvents such as dimethoxyethane, tetrahydrofuran and dioxane; carbonyl solvents such as acetone and methyl isobutyl ketone; alcohol solvents such as methanol and ethanol; 1,3-dimethyl-2-imidazolidone, N,N-dimethylformamide, dimethylsulfoxide, and mixtures thereof. The reaction is usually carried out at a temperature of 0° to 150° C., preferably 20° to 120° C., for 0.2 to 24 hours. The metal salt having Lewis acidity is usually used at a proportion of 0.01 to 20 moles, preferably 0.2 to 2 moles, taking into the consideration the effects on the post-treatment and reaction rate, to one mole of the thiourea derivative of the general formula [I]. The protonic acid is usually used at a proportion of 1 to 100 moles to one mole of the thiourea derivative of the general formula [I].

After completion of the reaction, water is added to the reaction mixture, which is then neutralized by addition of an alkali, and if necessary, followed by treatment such as filtration; the neutralized mixture is subjected to an ordinary post-treatment such as extraction with an organic solvent and concentration, and if necessary, any purification such as chromatography may be further utilized to give the desired 2-iminothiazoline derivative of the general formula [II].

In still another embodiment of the acid treatment according to the present invention, a 2-iminothiazoline derivative of the general formula [II] can be obtained by reaction of a thiourea derivative of the general formula [I] in the presence of a metal salt having Lewis acidity to give a 2-iminothiazolidine derivative of the general formula:

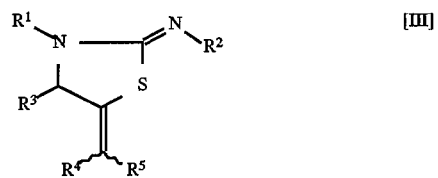

wherein $R^1$, $R^2$, $R^3$, $R^4$ and $R^5$ are each as defined above (the step is hereinafter referred to as "Reaction A") and by treatment of the 2-iminothiazolidine derivative of the general formula [III] with a protonic acid (the step is hereinafter referred to as "Reaction B").

Typical examples of the metal salt having Lewis acidity which can be used in Reaction A are stannic halides such as stannic chloride ($SnCl_4$), stannic bromide ($SnBr_4$) and stannic iodide ($SnI_4$); zinc halides such as zinc chloride ($ZnCl_2$), zinc bromide ($ZnBr_2$) and zinc iodide ($ZnI_2$); cupric halides such as cupric chloride ($CuCl_2$); and aluminum halides such as aluminum chloride ($AlCl_3$). These metal salts are not always required to be in anhydrous form, and they may contain crystal water.

Reaction A is usually carried out in a solvent. Typical examples of the solvent which can be used in the reaction are aliphatic hydrocarbon solvents such as heptane and hexane; aromatic hydrocarbon solvents such as benzene, toluene and xylene; halogenated hydrocarbon solvents such as monochlorobenzene, chloroform and ethylene dichloride; ether solvents such as dimethoxyethane, tetrahydrofuran and dioxane; carbonyl solvents such as acetone and methyl isobutyl ketone; alcohol solvents such as methanol and ethanol; 1,3-dimethyl-2-imidazolidone, N,N-dimethylformamide, dimethylsulfoxide, and mixtures thereof. Reaction A is usually carried out at a temperature of 0° to 150° C., preferably 50° to 120° C., for 0.2 to 24 hours. The metal salt having Lewis acidity is usually used at a proportion of 0.01 to 20 moles, preferably 0.2 to 2 moles, taking into the consideration the effects on the post-treatment and reaction rate, to one mole of the thiourea derivative of the general formula [I].

Typical examples of the protonic acid which can be used in Reaction B are inorganic acids such as hydrochloric acid and sulfuric acid; and organic acids such as methanesulfonic acid, trifluoroacetic acid and trifluoromethanesulfonic acid.

Reaction B is usually carried out in a solvent. Typical examples of the solvent which can be used in Reaction B are aliphatic hydrocarbon solvents such as heptane and hexane; aromatic hydrocarbon solvents such as benzene, toluene and xylene; halogenated hydrocarbon solvents such as monochlorobenzene, chloroform and ethylene dichloride; ether solvents such as dimethoxyethane, tetrahydrofuran and dioxane; carbonyl solvents such as acetone and methyl isobutyl ketone; alcohols such as methanol and ethanol; carboxylic acid solvents such as acetic acid and trifluoroacetic acid; 1,3-dimethyl-2-imidazolidone, N,N-dimethylformamide, dimethylsulfoxide, water, and mixtures thereof. Reaction B is usually carried out at a temperature of 0° to 150° C., preferably 20° to 100° C., for 0.2 to 24 hours. The protonic acid is usually used at a proportion of 1 to 100 moles to one mole of the 2-iminothiazolidine derivative of the general formula [III].

More specifically, in the treatment with a protonic acid, the isolated 2-iminothiazolidine derivative of the general formula [III] may be treated, or the reaction mixture after completion of the reaction of a thiourea derivative of the general formula [I] with a metal salt having Lewis acidity may be treated in the presence of the metal salt having Lewis acidity.

After completion of Reaction A or B, water is added to the reaction mixture, which is then neutralized by addition of an alkali, and if necessary, followed by treatment such as filtration; the neutralized mixture is subjected to an ordinary post-treatment such as extraction with an organic solvent and concentration, and if necessary, any purification such as chromatography may be further utilized to give the desired compound of the general formula [III] or [II].

The thiourea derivative of the general formula [I] used as a staring material in the present invention can be obtained, for example, by a process of the following scheme:

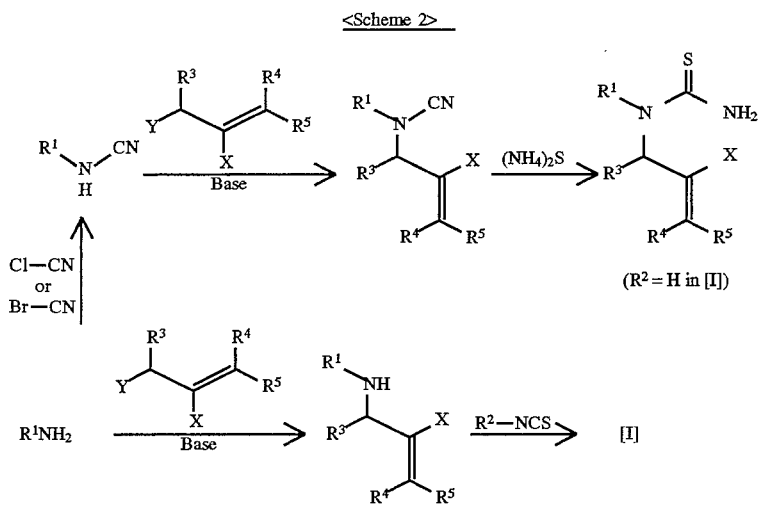

<Scheme 2> wherein $R^1, R^2, R^3, R^4, R^5$ and $R^6$ are each as defined above and Y is a leaving group such as chlorine, bromine, mesyloxy or tosyloxy.

The following Examples 1 to 11 will illustrate the process of producing 2-iminothiazoline derivatives according to the present invention, but these examples are not to be construed to limit the scope thereof.

The purity of a product was determined from the results of NMR spectroscopy and liquid chromatography. If the product exhibited no peaks of impurities in NMR spectroscopy and liquid chromatography, this product was determined to be pure.

The yield of a product was determined from the weight of the isolated product or by the external standard method using liquid chromatography (i.e., LC-ES method) or the internal standard method using gas chromatography (i.e., GC-IS method).

In the LC-ES method, the detection intensity of an isolated pure material, which was the same as a product to be measured, at a specified concentration was obtained by liquid chromatography; after completion of the reaction, the reaction mixture was adjusted to a specified concentration, and the detection intensity of the product was obtained by liquid chromatography; finally, the yield was calculated from both the detection intensities thus obtained. The liquid chromatography was carried out through a reverse-phase column ODS A 212 (manufactured by Sumika Chemical Analysis Service, Ltd.) with phosphate buffered aqueous solution (pH 7.2):methanol:tetrahydrofuran=40:55:5 as an eluent and an ultraviolet-visible absorption detector for detection at the wavelength of 254 nm.

In the GC-IS method, the detection intensity ratio of an isolated pure material, which was the same as a product to be measured, and an internal standard material (biphenyl) was obtained by gas chromatography; after completion of the reaction, a specified amount of the internal standard material was added to the reaction mixture, and the detection intensity ratio of the product and the internal standard material was obtained by gas chromatography; finally, the yield was calculated from both the detection intensity ratios thus obtained. The gas chromatography was carried out through a capillary column DB-1 having a wide bore (0.53 mm×30 m; manufactured by J & W Scientific) with helium gas as a carrier at a rate of 10 ml/min.

EXAMPLE 1

N-(3-(trifluoromethyl)phenyl)-N-(2-chloro-2-propenyl) thiourea (1.00 g) was added to 98% sulfuric acid (9.96 g) at room temperature with stirring, and the mixture was heated to 90° C. and stirred at the same temperature for 1.0 hour. After cooling, ice-water was added to the reaction mixture, which was then neutralized by addition of sodium carbonate and extracted with ethyl acetate. The organic layer was washed with water. The solvent was removed by distillation under reduced pressure, which afforded 0.835 g of 2-imino-3-(3-(trifluoromethyl)phenyl)-5-methyl-4-thiazoline as an oil (81% yield as a corrected value from the below-mentioned purity). From the results of analysis by liquid chromatography, the purity was determined to be 85%.

$^1$H-NMR (CDCl$_3$/TMS) δ (ppm): 7.9–7.5 (4H, m), 6.3 (1H, q), 5.3 (1H, br), 2.1 (3H, d).

Mass Spectrum (FD): Parent ion peak at (m/e) 258.

EXAMPLE 2

N-(3-(trifluoromethyl)phenyl)-N-(2-chloro-2-propenyl) thiourea (29.5 mg) was added to 90% sulfuric acid (1.0 ml) at room temperature with stirring, and the mixture was heated to 90° C. and stirred at the same temperature for 1 hour. After cooling, the reaction mixture was diluted with ice-water and acetonitrile to a specified concentration. With the LC-ES method, the yield of 2-imino-3-(3-(trifluoromethyl)phenyl)-5-methyl-4-thiazoline was determined to be 60%.

EXAMPLE 3

N-(3-(trifluoromethyl)phenyl)-N-(2-chloro-2-propenyl) thiourea (29.5 mg) was added to trifluoromethanesulfonic acid (1.0 ml) at room temperature with stirring, and the mixture was stirred at 25° C. for 1 hour. After cooling, the reaction mixture was diluted with ice-water and acetonitrile to a specified concentration. With the LC-ES method, the yield of 2-imino-3-(3-(trifluoromethyl)phenyl)-5-methyl-4-thiazoline was determined to be 86%.

EXAMPLE 4

N-(3,5-dichlorophenyl)-N-(2-chloro-2-propenyl)thiourea (0.30 g) was added to 90% sulfuric acid (3.5 g) at room temperature with stirring, and the mixture was heated to 90° C. and stirred at the same temperature for 1.0 hour. After cooling, water was added to the reaction mixture, which was then neutralized by addition of sodium hydrogen carbonate and extracted with ethyl acetate. The organic layer was washed with water. The solvent was removed by distillation under reduced pressure, and the residual oily material was subjected to column chromatography on silica gel, which afforded 0.16 g of 2-imino-3-(3,5-dichlorophenyl)-5-methyl-4-thiazoline (62% yield).

$^1$H-NMR (CDCl$_3$/TMS) δ (ppm): 7.4 (2H, d), 7.2 (1H, t), 6.3 (1H, q), 5.3 (1H, br), 2.0 (3H, d).

EXAMPLE 5

N-butyl-N-(2-chloro-2-propenyl)-N'-phenylthiourea (0.26 g) was added to 90% sulfuric acid (2.5 g) at room temperature with stirring, and the mixture was heated to 50° C. and stirred at the same temperature for 1.5 hour. After cooling, water was added to the reaction mixture, which was then neutralized by addition of sodium hydrogen carbonate and extracted with ethyl acetate. The organic layer was washed with water. The solvent was removed by distillation under reduced pressure, which afforded 0.09 g of 2-(N-phenylimino)-3-butyl-5-methyl-4-thiazoline as an oil (34% yield).

$^1$H-NMR (CDCl$_3$/TMS) δ (ppm): 7.4–7.2 (5H, m), 6.5 (1H, q), 4.1 (2H, t), 2.0 (3H, d), 1.8 (2H, tt), 1.4 (2H, tq), 1.0 (3H, t).

EXAMPLE 6

N-(3-(trifluoromethyl)phenyl)-N-(2-chloro-2-propenyl) thiourea (2.94 g) and zinc chloride (6.08 g) were added to xylene (50 ml) at room temperature, and the mixture was heated to 90° C. and stirred at the same temperature for 1.5 hour. After cooling, water was added to the reaction mixture, which was neutralized by addition of potassium hydrogen carbonate and extracted with ethyl acetate. The organic layer was washed with water. The solvent was removed by distillation under reduced pressure, and the residual oil was subjected to preparative liquid chromatography, which afforded 1.92 g of 2-imino-3-(3-(trifluoromethyl)phenyl)-5-methylidenethiazolidine (74% yield). From the results of analysis by liquid chromatography, the purity was determined to be not lower than 99%.

$^1$H-NMR (CDCl$_3$/TMS) δ (ppm): 7.9–7.3 (4H, m), 6.9 (1H, br), 5.3 (1H, dd), 5.1 (1H, dd), 4.6 (2H, t).

Mass Spectrum (FD): Parent ion peak at (m/e) 258.

The 2-imino-3-(3-(trifluoromethyl)phenyl)-5-methylidenethiazolidine thus obtained (29.4 mg) was added to 90% sulfuric acid (0.5 ml), and the mixture was heated to 40° C. and stirred at the same temperature for 1 hour. After cooling, the reaction mixture was neutralized by addition of sodium hydrogen carbonate and extracted with ethyl acetate. The organic layer was washed with water and concentrated by distillation of the solvent under reduced pressure. The concentrate was dissolved together with biphenyl in acetonitrile. With the GC-IS method, the yield of 2-imino-3-(3-(trifluoromethyl)phenyl)-5-methyl-4-thiazoline was determined to be 98% (on the basis of 2-imino-3-(3-trifluoromethyl)phenyl)-5-methylidenethiazolidine).

The 2-imino 3-(3-(trifluoromethyl)phenyl)-5-methylidenethiazolidine thus obtained (29.4 mg) was added to 35% hydrochloric acid (0.5 ml), and the mixture was heated to 40° C. and stirred at the same temperature for 1 hour. After cooling, the reaction mixture was neutralized by addition of sodium hydrogen carbonate and extracted with ethyl acetate. The organic layer was washed with water and concentrated by distillation of the solvent under reduced pressure. The concentrate was dissolved together with biphenyl in acetonitrile. With the GC-IS method, the yield of 2-imino-3-(3-(trifluoromethyl)phenyl)-5-methyl-4-thiazoline was determined to be 96% (on the basis of 2-imino-3-(3-(trifluoromethyl)phenyl)-5-methylidenethiazolidine).

EXAMPLE 7

N-(3-(trifluoromethyl)phenyl)-N-(2-chloro-2-propenyl) thiourea (29 mg) and zinc bromide (63 mg) were added to xylene (about 2 g) at room temperature, and the mixture was heated to 90° C. and stirred at the same temperature for 1 hour. After cooling, the reaction mixture was diluted with water and acetonitrile to a specific concentration. With the LC-ES method, the yield of 2-imino-3-(3-(trifluoromethyl) phenyl)-5-methylidenethiazolidine was determined to be 85%.

The 2-imino-3-(3-(trifluoromethyl)phenyl)-5-methylidenethiazolidine thus obtained is converted into 2-imino-3-(3-(trifluoromethyl)phenyl)-5-methyl-4-thiazoline in the same manner as described in the latter half of Example 9.

EXAMPLE 8

N-(3-(trifluoromethyl)phenyl)-N-(2-chloro-2-propenyl) thiourea (294 mg) and anhydrous stannic chloride (24 μl) were added to trifluoroacetic acid (1.0 ml) at room temperature, and the mixture was heated to 75° C. and stirred at the same temperature for 3 hours. After cooling, water was added to the reaction mixture, neutralized by addition of sodium hydrogen carbonate, and diluted with acetonitrile to a specified concentration. With the LC-ES method, the yield of 2-imino-3-(3-(trifluoromethyl)phenyl) -5-methyl-4-thiazoline was determined to be 84%.

EXAMPLE 9

N-(3-(trifluoromethyl)phenyl)-N-(2-chloro-2-propenyl) thiourea (1.47 g) and stannic chloride n-hydrate (n=4 to 5) (0.09 g) were added to methyl isobutyl ketone (7.50 g) at room temperature, and the mixture was heated to 90° C. and stirred at the same temperature for 7 hours. After cooling, 35% hydrochloric acid (0.52 g) was added to the reaction mixture with stirring, and the mixture was heated to 90° C. and stirred at the same temperature for 2.5 hours. After cooling, water was added to the reaction mixture, which was then neutralized by addition of sodium hydrogen carbonate and extracted with methyl isobutyl ketone. The organic layer was washed with water. The solvent was removed by distillation under reduced pressure, which afforded 1.08 g of 2-imino-3-(3-(trifluoromethyl)phenyl)-5-methyl-4-thiazoline (75% yield as a corrected value from the below-mentioned purity). From the results of analysis by liquid chromatography, the purity was determined to be 89%.

EXAMPLE 10

N-(3-(trifluoromethyl)phenyl)-N-(2-chloro-2-propenyl) thiourea (295 mg) and zinc chloride (64 mg) were added to methyl isobutyl ketone (2.50 g) at room temperature, followed by addition of 35% hydrochloric acid (100 mg) at room temperature with stirring, and the mixture was heated to 90° C. and stirred at the same temperature for 9 hours. After cooling, zinc chloride (137 mg) was further added to the reaction mixture with stirring, and the mixture was heated to 90° C. and stirred at the same temperature for 2 hours. After cooling, the reaction mixture was diluted with acetonitrile to a specified concentration. With the LC-ES method, the yield of 2-imino-3-(3-(trifluoromethyl)phenyl) -5-methyl-4-thiazoline was determined to be 65%.

EXAMPLE 11

N-(4-methoxyphenyl)-N-(2-chloro-2-propenyl)thiourea (0.26 g) and stannic chloride n-hydrate (n=4 to 5; 0.14 g) were added to 1,3-dimethyl-2-imidazolidone (2.50 g) at room temperature with stirring, and the mixture was heated to 90° C. and stirred at the same temperature for 1 hour. Then, 35% hydrochloric acid (0.16 g) was added to the reaction mixture at 90° C. with stirring, and the mixture was stirred at 90° C. for 11 hours. After cooling, water was added to the reaction mixture, which was then neutralized by addition of sodium hydrogen carbonate and extracted with methyl isobutyl ketone. The organic layer was washed with water. The solvent was removed by distillation under reduced pressure, which afforded 0.28 g of an oily mixture of 2-imino-3-(4-methoxyphenyl)-5-methyl-4-thiazoline and 1,3-dimethyl-2-imidazolidone. With $^1$H-NMR spectroscopy, the yield of 2-imino-3-(4-methoxyphenyl)-5-methyl-4-thiazoline was determined to be 53%.

EXAMPLE 12

A mixture of N-(3-(trifluoromethyl)phenyl)-N-(2-chloro-2-propenyl)cyanamide (168.67 g), methyl isobutyl ketone ((674.70 g) and ammonium sulfide solution, yellow (518.77 g) having an S content of 6% was stirred at 50° C. for 9 hours. After cooling to 20° C., water (1774.70 g) was poured into the reaction mixture, which was then shaken and fractionated with a separatory funnel. The water layer was extracted twice with methyl isobutyl ketone (53.72 g×2). The combined methyl isobutyl ketone layer was washed with water (81.05 g) to give a methyl isobutyl ketone solution (938.58 g) of N-(3-(trifluoromethyl)phenyl)-N-(2-chloro-2-propenyl)thiourea.

To this solution (938.58 g), stannic chloride n-hydrate (n=4 to 5) (19.00 g) was added, and the mixture was stirred at 90° C. for 9 hours. After cooling below 30° C., 15% aqueous NaOH solution (150 g) was added to the reaction mixture, which was then stirred and fractionated with a separatory funnel. The methyl isobutyl ketone layer was washed with saturated aqueous NaCl solution (200 g), followed by fractionation with a separatory funnel, which afforded a methyl isobutyl ketone solution (915.32 g) of 2-imino-3-(3-(trifluoromethyl)phenyl)-5-methyl-4-thiazoline.

To this solution (915.32 g), 35% aqueous HCl solution (93.5 g) was added, and the mixture was heated to 95° C. Water was removed by azeotropic distillation, and methyl isobutyl ketone (615.30 g) was removed by distillation, after which the remaining methyl isobutyl ketone solution was gradually cooled to 20° C. The resulting crystals were filtered and washed with methyl isobutyl ketone (110 g) cooled below 5° C., which afforded 2-imino-3-(3-(trifluoromethyl)phenyl)-5-methyl-4-thiazoline hydrochloride (64% yield on the basis of N-(3-(trifluoromethyl) phenyl)-N-(2-chloro-2-propenyl)cyanamide).

The present invention also provides a process of producing N-substituted N-arylcyanamide derivatives and a process of producing N-substituted N-arylthiourea derivatives, both of which derivatives are useful as some intermediates for the production of 2-iminothiazoline derivatives of the general formula [I] as depicted above.

As a conventional process of producing N-substituted N-arylcyanamide derivatives, there is, for example, a process of the following scheme as described in J. Org. Chem., 29, 153–157 (1964):

<Scheme 3>

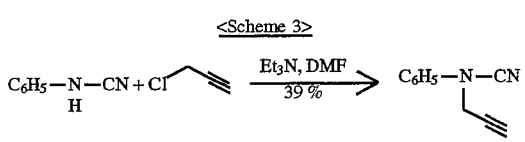

wherein Et$_3$N is triethylamine and DMF is N,N-dimethylformamide.

Even if this process is employed, however, N-substituted N-arylcyanamide derivatives cannot be obtained in satisfactory yield as shown in the above scheme.

The present inventors have intensively studied various production processes for N-substituted N-arylcyanamide derivatives of the general formula [VI] as depicted below and N-substituted N-arylthiourea derivative of the general formula [VII] as depicted below with industrial benefit. As the result, they have found that N-substituted N-arylcyanamide derivatives of the general formula [VI] as depicted below can be obtained with high purity in high yield by reacting N-arylcyanamide derivatives of the general formula [IV] as depicted below with allyl halide derivatives of the general formula [V] in an aprotic polar solvent in the presence of an iodide and an alkali metal carbonate, and that N-substituted N-arylthiourea derivatives of the general formula [VII] as depicted below can be obtained with high purity in high yield by reacting an N-substituted N-cyanamide derivatives as obtained above with a chemical species which generates sulfide ion or hydrogensulfide ion (e.g., hydrogen sulfide; ammonium sulfide ((NH$_4$)$_2$S$_n$: the mole ratio of NH$_3$ and H$_2$S may vary in value, such as n=1, 3); sulfur (S$_8$) and ammonia; sulfur and organic amine).

Thus, the present invention also provides a process of producing an N-substituted N-arylcyanamide derivative of the general formula:

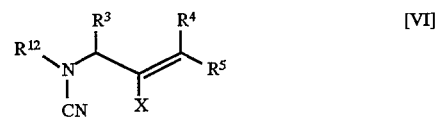

[VI]

wherein R$^3$, R$^4$, R$^5$ and X are each as defined above and R$^{12}$ is optionally substituted aryl, the process comprising the step of reacting an N-arylcyanamide derivative of the general formula:

[IV]

wherein R$^{12}$ is as defined above, with an allyl halide derivative of the general formula:

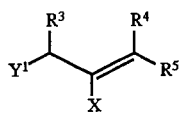

wherein $R^3$, $R^4$, $R^5$ and X are each as defined above and $Y^1$ is chlorine or bromine, in an aprotic polar solvent in the presence of an iodide and an alkali metal carbonate.

Further provided is a process of producing an N-substituted N-arylthiourea derivative of the general formula:

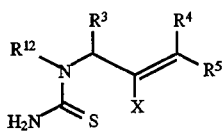

wherein $R^3$, $R^4$, $R^5$, $R^{12}$ and X are each as defined above, the process comprising the step of reacting an N-substituted N-arylcyanamide derivative of the general formula:

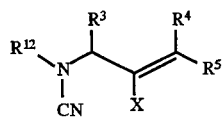

wherein $R^3$, $R^4$, $R^5$, $R^{12}$ and X are each as defined above, with a chemical species which generates sulfide ion or hydrogensulfide ion.

In the present invention, typical examples of the $R^{12}$ are aryl optionally substituted with at least one substituent (e.g., $C_{1-8}$ alkyl optionally substituted with at least one halogen; $C_{1-8}$ alkoxy optionally substituted with at least one halogen; aryl, nitro, halogen, etc.).

Specific examples of the N-aryl-cyanamide derivative of the general formula [IV] used as a starting material in the present invention are as follows:
3-(trifluoromethyl)phenylcyanamide;
3-(trifluoromethoxy)phenylcyanamide;
4-fluoro-3-(trifluoromethyl)phenylcyanamide;
3,5-dichlorophenylcyanamide;
4-methoxyphenylcyanamide; and
2-chlorophenylcyanamide.

Specific examples of the allyl halide derivative of the general formula [V] are as follows:
2,3-dichloro-1-propene;
2,3-dichloro-3-methyl-1-propene;
1,2-dichloro-2-butene;
1,2-dichloro-3-methyl-2-butene; and
2,3-dibromo-1-propene.

Specific examples of the N-substituted N-arylcyanamide derivative of the general formula [VI] are as follows:
N-(3-(trifluoromethyl)phenyl)-N-(2-chloro-2-propenyl) cyanamide;
N-(3-(trifluoromethyl)phenyl)-N-(2-chloro-1-methyl-2-propenyl)cyanamide;
N-(3-(trifluoromethyl)phenyl)-N-(2-chloro-2-butenyl) cyanamide;
N-(3-(trifluoromethyl)phenyl)-N-(2-chloro-3-methyl-2-butenyl)cyanamide;
N-(3-(trifluoromethyl)phenyl)-N-(2-bromo-2-propenyl) cyanamide;
N-(3-(trifluoromethoxy)phenyl)-N-(2-chloro-2-propenyl) cyanamide;
N-(3-(trifluoromethoxy)phenyl)-N-(2-chloro-1-methyl-2-propenyl)cyanamide;
N-(3-(trifluoromethoxy)phenyl)-N-(2-chloro-2-butenyl) cyanamide;
N-(3-(trifluoromethoxy)phenyl)-N-(2-chloro-3-methyl-2-butenyl)cyanamide;
N-(4-fluoro-3-(trifluoromethyl)phenyl)-N-(2-chloro-2-propenyl)cyanamide;
N-(4-fluoro-3-(trifluoromethyl)phenyl)-N-(2-chloro-1-methyl-2-propenyl)cyanamide;
N-(4-fluoro-3-(trifluoromethyl)phenyl)-N-(2-chloro-2-butenyl)cyanamide;
N-(4-fluoro-3-(trifluoromethyl)phenyl)-N-(2-chloro-3-methyl-2-butenyl)cyanamide;
N-(3,5-dichlorophenyl)-N-(2-chloro-2-propenyl) cyanamide;
N-(4-methoxyphenyl)-N-(2-chloro-2-propenyl)cyanamide; and
N-(2-chlorophenyl)-N-(2-chloro-2-propenyl)cyanamide.

Specific examples of the N-substituted N-arylthiourea derivatives of the general formula [VII] are as follows:
N-(3-(trifluoromethyl)phenyl)-N-(2-chloro-2-propenyl) thiourea;
N-(3-(trifluoromethyl)phenyl)-N-(2-chloro-1-methyl-2-propenyl)thiourea;
N-(3-(trifluoromethyl)phenyl)-N-(2-chloro-2-butenyl) thiourea;
N-(3-(trifluoromethyl)phenyl)-N-(2-chloro-3-methyl-2-butenyl)thiourea;
N-(3-(trifluoromethyl)phenyl)-N-(2-bromo-2-propenyl) thiourea;
N-(3-(trifluoromethoxy)phenyl)-N-(2-chloro-2-propenyl) thiourea;
N-(3-(trifluoromethoxy)phenyl)-N-(2-chloro-1-methyl-2-propenyl)thiourea;
N-(3-(trifluoromethoxy)phenyl)-N-(2-chloro-2-butenyl) thiourea;
N-(3-(trifluoromethoxy)phenyl)-N-(2-chloro-3-methyl-2-butenyl)thiourea;
N-(4-fluoro-3-(trifluoromethyl)phenyl)-N-(2-chloro-2-propenyl)thiourea;
N-(4-fluoro-3-(trifluoromethyl)phenyl)-N-(2-chloro-1-methyl-2-propenyl)thiourea;
N-(4-fluoro-3-(trifluoromethyl)phenyl)-N-(2-chloro-2-butenyl)thiourea;
N-(4-fluoro-3-(trifluoromethyl)phenyl)-N-(2-chloro-3-methyl-2-butenyl)thiourea;
N-(3,5-dichlorophenyl)-N-(2-chloro-2-propenyl)thiourea;
N-(4-methoxyphenyl)-N-(2-chloro-2-propenyl)thiourea; and
N-(2-chlorophenyl)-N-(2-chloro-2-propenyl)thiourea.

Typical examples of the alkali metal carbonate used in the reaction of N-arylcyanamide derivative of the general formula [IV] with the allyl halide derivative of the general formula [V] to form the N-substituted N-arylcyanamide derivative of the general formula [VI] are sodium carbonate and potassium carbonate. In usual cases, powder of alkali metal carbonate is used; when fine powder of alkali metal carbonate having a wider surface area per specified weight (e.g., having a particle size of 30 mesh or less) is used, the reaction rate will become further high.

Typical examples of the iodide are alkali metal iodides such as sodium iodide and potassium iodide; and alkaline earth metal iodides such as calcium iodide and barium iodide. Sodium iodide or potassium iodide is usually used.

As the aprotic polar solvent, preferred are those having a relative permittivity of 22 or more. Specific examples thereof are N,N-dimethylformamide (DMF), dimethylsulfoxide (DMSO), hexamethylphosphoric triamide (HMPA), sulfolane, N-metylpyrrolidone (NMP), N,N'-dimethylpropyleneurea (DMPU), 1,3-dimethyl-2-imidazolidinone (DMI), nitromethane, acetonitrile, N,N- dimethylacetamide (DMA), and mixtures thereof. DMF, DMSO and NMP are particularly preferred from an industrial point of view.

As the allyl halide derivative of the general formula [V], those having bromine in X are higher reactive and make the reaction time short, whereas those having chlorine in X are readily available at a small cost, which is more favorable for practical use.

The reaction is usually carried out at a temperature of 0° to 150° C., preferably 20° to 80° C., for 0.5 to 24 hours. The alkali metal carbonate and the iodide are usually used at a proportion of 0.5 to 3 moles and 0.01 to 1.0 mole, respectively, to one mole of the compound of the general formula [IV].

After completion of the reaction, the reaction mixture is concentrated as the case may be, and water is added, and if necessary, the mixture is neutralized by addition of an acid such as diluted hydrochloric acid; the neutralized mixture is subjected to an ordinary post-treatment such as extraction with an organic solvent and concentration, and if necessary, any purification such as chromatography may be further utilized to give the desired N-substituted N-arylcyanamide derivative of the general formula [VI].

The reaction for conversion of the N-substituted N-arylcyanamide derivative of the general formula [VI] into the N-substituted N-arylthiourea derivative of the general formula [VII] can be carded out, for example, by the following procedures:

(a) Hydrogen sulfide gas and ammonia gas are blown at the same rate into a solution of the N-substituted N-arylcyanamide derivative of the general formula [VI];

(b) Hydrogen sulfide gas is blown into or sulfur is added to a solution of the N-substituted N-arylcyanamide derivative of the general formula [VI] and ammonia water;

(c) Hydrogen sulfide gas is blown into or sulfur is added to a solution of the N-substituted N-arylcyanamide derivative of the general formula [VI] and an organic amine (e.g., triethylamine, pyridine, aniline, morpholine, etc.); or (d) A solution of the N-substituted N-arylcyanamide derivative of the general formula [VI] is brought together with an ammonium sulfide solution.

The above reactions (a) to (d) are usually carried out in a solvent. Typical example of the solvent which can be in these reactions, although they are not particularly limited, are aromatic hydrocarbon solvents such as benzene, toluene and xylene; halogenated hydrocarbon solvents such as monochlorobenzene, chloroform and ethylene dichloride; ether solvents such as dimethoxyethane, tetrahydrofuran and dioxane; carbonyl solvents such as acetone and methyl isobutyl ketone; alcohols such as methanol and ethanol; N,N-dimethylformamide (DMF, dimethylsulfoxide (DMSO), water, and mixtures thereof. These reactions are usually carried out at a temperature of 0° to 150° C. for 0.2 to 24 hours. Hydrogen sulfide, sulfur or ammonium sulfide (as an S content) was used at a proportion of 1.0 to 5 moles, preferably 1.2 to 2 moles, to one mole of the N-substituted N-arylcyanamide derivative of general formula [VI]. Also in the reactions (a) to (c), ammonia or an organic amine is used at a proportion of 0.1 to 1.2 moles to one mole of hydrogen sulfide, sulfur or ammonium sulfide.

The above reactions may be carded out by using the isolated N-substituted N-arylcyanamide derivative of the general formula [VI] or by using the reaction mixture, without further treatment, after completion of the reaction of the N-arylcyanamide derivative of the general of formula [IV] with the allyl halide derivative of the general formula [V] to form the N-substituted N-arylcyanamide derivative of the general formula [VI].

After completion of the reaction, the reaction mixture is concentrated as the case may be, and water is added, and if necessary, the mixture is neutralized by addition of an acid such as diluted hydrochloric acid; the neutralized mixture is subjected to an ordinary post-treatment such as extraction with an organic solvent and concentration, and if necessary, any purification such as chromatography may be further utilized to give the desired N-substituted N-arylthiourea derivative of the general formula [VII].

The N-arylcyanamide derivative [IV] used as a starting material in the present invention can be obtained by the conventional method. Also the allyl halide derivative of the general formula [V] is commercially available or can be obtained by the conventional method.

The following Examples 13 to 16 will illustrate a process of producing N-substituted N-arylcyanamide derivatives and a process of producing N-substituted N-arylthiourea derivatives according to the present invention, but these examples are not to be construed to limit the scope thereof.

The purity of a product was determined from the results of NMR spectroscopy and gas chromatography and/or liquid chromatography.

The gas chromatography was carded out through a capillary column DB-1 having a wide bore (manufactured by J & W Scientific) with a flame ionization detector for detection.

The liquid chromatography was carried out through a reverse-phase column ODS A 212 (manufactured by Sumika Chemical Analysis Service, Ltd.) with phosphate buffered aqueous solution (pH 7.2):methanol:tetrahydrofuran= 40:55:5 as an eluent and an ultraviolet-visible absorption detector for detection at the wavelength of 254 nm.

EXAMPLE 13

N-(3-(trifluoromethyl)phenyl)cyanamide (18.6 g) was dissolved in N,N-dimethylformamide (DMF) (93.0 g), to which powdered potassium carbonate (20.7 g) and potassium iodide (1.7 g) were added at room temperature with stirring. Further, 2,3-dichloro-1-propene (13.3 g) was added dropwise at room temperature with stirring. The mixture was heated to 50° C. and stirred at the same temperature for 1 hour. After cooling to room temperature, waster was added to the reaction mixture, which was then extracted with ethyl acetate. The organic layer was washed with water. The solvent was removed by distillation under reduced pressure, which afforded 25.8 g of N-(3-(trifluoromethyl)phenyl)-N-(2-chloro-2-propenyl)cyanamide as an oil (99% yield in appearance). The percentage areas of gas chromatography and liquid chromatography were 98% and 99%, respectively.

$^1$H-NMR (CDCl$_3$/TMS) δ (ppm): 7.8–7.3 (4H, m), 5.6 (2H, s), 4.4 (2H, s).

Mass Spectrum (EI): Parent ion peak at (m/e) 260.

The N-(3-(trifluoromethyl)phenyl-N-(2-chloro-2-propenyl)cyanamide thus obtained (23.2 g) was dissolved in ethanol (380 ml), to which aqueous ammonium sulfide solution, colorless (460.8 g) having an S content of 0.6% was added dropwise at room temperature with stirring. The mixture was heated to 50° C. and stirred at the same temperature for 8 hours. After cooling to room temperature, ethanol was removed by distillation under reduced pressure, and the residue was extracted with ethyl acetate. The organic layer was washed with water. The solvent was removed by distillation under reduced pressure, which afforded 25.2 g of N-(3-(trifluoromethyl)phenyl)-N-(2-chloro-2-propenyl) thiourea as a solid (96% yield in appearance). The percentage areas of gas chromatography and liquid chromatography were 99% and 100%, respectively.

$^1$H-NMR (CDCl$_3$/TMS) δ (ppm): 7.8–7.6 (4H, m), 5.9 (2H, br), 5.4 (1H, s), 5.4 (1H, s), 5.1 (2H, s).

Mass Spectrum (FD): Parent ion peak at (m/e) 294.

EXAMPLE 14

N-(3-(trifluoromethyl)phenyl)cyanamide (16.3 g) was dissolved in DMF (108.6 g), to which powdered potassium carbonate (18.4 g) was added at room temperature with stirring. Further, 2,3-dichloro-1-propene (11.8 g) was added dropwise at room temperature with stirring. The mixture was heated to 50° C. and stirred at the same temperature for 1.5 hours. (The percentage area ratio of N-(3-(trifluoromethyl)phenyl)cyanamide and N-(3-(trifluoromethyl)phenyl)-N-(2-chloro-2-propenyl)cyanamide in liquid chromatography of the reaction mixture after one hour from the temperature rise was 81:19). Then, potassium iodide (1.7 g) was added at 50° C. with stirring, and the mixture was stirred at the same temperature for 1.5 hour. (The percentage area ratio of N-(3-(trifluoromethyl)phenyl)cyanamide and N-(3-(trifluoromethyl)phenyl)-N-(2-chloro-2-propenyl) cyanamide in liquid chromatography of the reaction mixture after one hour from the iodide addition was 1:99). After cooling to room temperature, water was added to the reaction mixture, which was then extracted with ethyl acetate. The organic layer was washed with water. The solvent was removed by distillation under reduced pressure, which afforded 23.3 g of N-(3-trifluoromethyl)phenyl)-N-(2-chloro-2-propenyl)cyanamide as an oil (100% yield in appearance). The percentage area of gas chromatography was 92%.

The N-(3-(trifluoromethyl)phenyl-N-(2-chloro-2-propenyl)cyanamide thus obtained (2.62 g) was dissolved in methanol (13.25 g), to which ammonium sulfide solution, yellow (8.17 g) having an S content of 6% was added dropwise at room temperature with stirring. The mixture was heated to 50° C. and stirred at the same temperature for 7 hours. After cooling to room temperature, water was added to the reaction mixture, which was then extracted with ethyl acetate. The organic layer was washed with water. The solvent was removed by distillation under reduced pressure, which afforded 2.82 g of N-(3-(trifluoromethyl)phenyl)-N-(2-chloro-2-propenyl)thiourea (95% yield in appearance). The percentage area of gas chromatography was 86%.

The N-(3-(trifluoromethyl)phenyl)-N-(2-chloro-2-propenyl)cyanamide (2.61 g) was dissolved in methyl isobutyl ketone (13.01 g), to which ammonium sulfide solution, yellow (8.12 g) having an S content of 6% was added dropwise at room temperature with stirring. The mixture was heated to 50° C. and stirred at the same temperature for 9 hours. After cooling to room temperature, water was added to the reaction mixture, which was then extracted with ethyl acetate. The organic layer was washed with water. The solvent was removed by distillation under reduced pressure, which afforded 2.67 g of N-(3-(trifluoromethyl)phenyl)-N-(2-chloro-2-propenyl)thiourea as a solid (90% yield in appearance). The percentage area of gas chromatography was 85%.

A mixture of the N-(3-(trifluoromethyl)phenyl)-N-(2-chloro-2-propenyl)cyanamide (0.8 g), sulfur (S$_8$) (0.15 g), methyl isobutyl ketone (5 ml) and about 30% ammonia water (4 ml) was stirred at 50° C. for 6 hours. Water (20 ml) was added to the reaction mixture, which was then extracted twice with ethyl acetate (30 ml×2). The solvent was removed by distillation under reduced pressure, and the resulting crystals were washed with hexane, which afforded 0.77 g of N-(3-(trifluoromethyl)phenyl)-N-(2-chloro-2-propenyl)thiourea (85% yield).

EXAMPLE 15

N-(3,5-dichlorophenyl)cyanamide (2.81 g) was dissolved in DMF (14.03 g), to which powdered potassium carbonate (3.11 g) and potassium iodide (0.26 g) were added at room temperature with stirring. Further, 2,3-dichloro-1-propene (2.00 g) was added dropwise at room temperature with stirring. The mixture was heated to 50° C. and stirred at the same temperature for 2.5 hours. After cooling to room temperature, DMF (9.00 g) and ammonium sulfide solution, yellow (8.00 g) having an S content of 6% were added dropwise to the reaction mixture at room temperature with stirring. The mixture was heated to 50° C. and stirred at the same temperature for 4 hour. After cooling to room temperature, water was added to the reaction mixture, which was then extracted with ethyl acetate. The organic layer was washed with water. The solvent was removed by distillation under reduced pressure, which afforded 4.00 g of N-(3,5-dichlorophenyl)-N-(2-chloro-2-propenyl)thiourea as a dark red solid (90% yield in appearance). The percentage area of liquid chromatography was 94%.

$^1$H-NMR (CDCl$_3$/TMS) δ (ppm): 7.5 (1H, t), 7.3 (2H, d), 5.8 (2H, br), 5.4 (1H, s), 5.3 (1H, s), 5.1 (2H, s).

EXAMPLE 16

N-(4-methoxyphenyl)cyanamide (2.22 g) was dissolved in DMF (11.10 g), to which powdered potassium carbonate (3.11 g) and potassium iodide (0.26 g) were added at room temperature with stirring. Further, 2,3-dichloro-1-propene (2.00 g) was added dropwise at room temperature with stirring. The mixture was heated to 50° C. and stirred at the same temperature for 1.5 hours. After cooling to room temperature, ammonium sulfide solution, yellow (8.00 g) having an S content of 6% were added dropwise to the reaction mixture at room temperature with stirring. The mixture was heated to 50° C. and stirred at the same temperature for 3 hour. After cooling to room temperature, water was added to the reaction mixture, which was then extracted with ethyl acetate. The organic layer was washed with water. The solvent was removed by distillation under reduced pressure, which afforded 3.63 g of N-(4-methoxyphenyl)-N-(2-chloro-2-propenyl)thiourea as a dark red solid (94% yield in appearance). The percentage area of liquid chromatography was 94%.

$^1$H-NMR (CDCl$_3$/TMS) δ (ppm): 7.2 (2H, d), 7.0 (2H, d), 5.7 (2H, br), 5.3 (1H, s), 5.3 (1H, s), 5.1 (2H, s), 3.9 (3H, s).

COMPARATIVE EXAMPLE 1

N-(3-(trifluoromethyl)phenyl)cyanamide (5.58 g) was dissolved in toluene (90.0 g), to which powdered potassium carbonate (6.22 g), potassium iodide (0.50 g) and tetrabutylammonium bromide (0.97 g) were added at room temperature with stirring. Further, 2,3-dichloro-1-propene (4.00 g) was added dropwise at room temperature with stirring. The mixture was heated to 80° C. and stirred at the same temperature for 7 hours. After it was confirmed that N-(3-(trifluoromethyl)phenyl)cyanamide disappeared, the reaction mixture was cooled to room temperature, and water was added to the reaction mixture, which was then extracted with ethyl acetate. The organic layer was washed with water. The solvent was removed by distillation under reduced pressure, which afforded 7.44 g of crude N-(3-trifluoromethyl)phenyl) -N-(2-chloro-2-propenyl)cyanamide as an oil (95% yield in appearance). The percentage area of liquid chromatography was 55%.

COMPARATIVE EXAMPLE 2

N-(3-(trifluoromethyl)phenyl)cyanamide (5.58 g) was dissolved in methyl isobutyl ketone (90.0 g), to which powdered potassium carbonate (6.22 g), potassium iodide (0.50 g) and tetrabutylammonium bromide (0.97 g) were added at room temperature with stirring. Further, 2,3-dichloro-1-propene (4.00 g) was added dropwise at room temperature with stirring. The mixture was heated to 80° C. and stirred at the same temperature for 7 hours. After it was confirmed that N-(3-(trifluoromethyl)phenyl)cyanamide disappeared, the reaction mixture was cooled to room temperature, and water was added to the reaction mixture, which was then extracted with ethyl acetate. The organic layer was washed with water. The solvent was removed by distillation under reduced pressure, which afforded 8.21 g of crude N-(3-trifluoromethyl)phenyl)-N-(2-chloro-2-propenyl)cyanamide as an oil (105% yield in appearance). The percentage area of liquid chromatography was 42%.

COMPARATIVE EXAMPLE 3

N-(3-(trifluoromethyl)phenyl)cyanamide (2.79 g) was dissolved in acetone (45.0 g), to which powdered potassium carbonate (3.11 g), potassium iodide (0.25 g) and benzyltriethylammonium chloride (0.34 g) were added at room temperature with stirring. Further, 2,3-dichloro-1-propene (2.00 g) was added dropwise at room temperature with stirring. The mixture was heated to 50° C. and stirred at the same temperature for 6 hours. After it was confirmed that N-(3-(trifluoromethyl)phenyl)cyanamide disappeared, the reaction mixture was cooled to room temperature, and water was added to the reaction mixture, which was then extracted with ethyl acetate. The organic layer was washed with water, which afforded a solution of crude N-(3-trifluoromethyl)phenyl)-N-(2-chloro-2-propenyl)cyanamide. The percentage area of liquid chromatography was 35%.

As described in the former half of Example 13, in the reaction of an N-arylcyanamide derivative of the general formula [IV] with an allyl halide derivative of the general formula [V] to form an N-substituted N-arylcyanamide derivative of the general formula [VI], the reaction rate was remarkably reduced in cases where no iodide was added to the reaction system. As described in Comparative Examples 1 to 3, the reaction rate was also reduced and the product, N-substituted N-arylcyanamide derivative of the general formula [VI], had a decreased purity in cases where the reaction was carried out in a solvent such as toluene, methyl isobutyl ketone or acetone.

What is claimed is:

1. A thiourea derivative of the general formula:

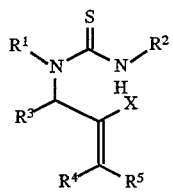

(I)

wherein $R^1$ is a $C_6$–$C_{10}$ aryl or heteroaryl group unsubstituted or substituted with at least one substituent selected from $C_6$–$C_{10}$ aryl, nitro, halogen, $C_1$–$C_8$ alkyl unsubstituted or substituted with at least one hydrogen atom, and $C_1$–$C_8$ alkoxy unsubstituted or substituted with at least one halogen atom; and wherein $R^2$ is hydrogen; $C_1$–$C_8$ alkyl unsubstituted or substituted with at least one substituent selected from $C_1$–$C_8$ alkoxy and $C_3$–$C_8$ cycloalkyl; $C_3$–$C_8$ cycloalkyl unsubstituted or substituted with at least one substituent selected from $C_1$–$C_8$ alkyl, $C_1$–$C_8$ alkoxy and $C_6$–$C_{10}$ aryl; $C_6$–$C_{10}$ aryl unsubstituted or substituted with at least one substituent selected from $C_6$–$C_{10}$ aryl, nitro, halogen, $C_1$–$C_8$ alkyl and $C_1$–$C_8$ alkoxy; $C_1$–$C_8$ alkylcarbonyl unsubstituted or substituted with at least one substituent selected from $C_1$–$C_8$ alkoxy, $C_6$–$C_{10}$ aryl and $C_3$–$C_8$ cycloalkyl; $C_3$–$C_8$ cycloalkylcarbonyl unsubstituted or substituted with at least one substituent selected from $C_1$–$C_8$ alkyl, $C_1$–$C_8$ alkoxy and $C_6$–$C_{10}$ aryl; a phenylcarbonyl, α-naphthylcarbonyl or β-naphthylcarbonyl group unsubstituted or substituted with at least one substituent selected from $C_1$–$C_8$ alkyl, $C_1$–$C_8$ alkoxy and $C_6$–$C_{10}$ aryl; $C_1$–$C_8$ alkoxycarbonyl unsubstituted or substituted with at least one substituent selected from $C_1$–$C_8$ alkoxy, $C_6$–$C_{10}$ aryl and $C_3$–$C_8$ cycloalkyl; $C_3$–$C_8$ cycloalkyloxycarbonyl unsubstituted or substituted with at least one substituent selected from $C_1$–$C_8$ alkyl, $C_1$–$C_8$ alkoxy and $C_6$–$C_{10}$ aryl; or a phenoxycarbonyl, α-naphthoxycarbonyl or β-naphthoxycarbonyl group unsubstituted or substituted with at least one substituent selected from $C_6$–$C_{10}$ aryl, nitro, halogen, $C_1$–$C_8$ alkyl unsubstituted or substituted with at least halogen atom, and $C_1$–$C_8$ alkoxy unsubstituted or substituted with at least one halogen atom; and $R^3$, $R^4$ and $R^5$ are the same or different, each of which is hydrogen; $C_1$–$C_8$ alkyl unsubstituted or substituted with at least one substituent selected from $C_1$–$C_8$ alkoxy, $C_3$–$C_8$ cycloalkyl and $C_6$–$C_{10}$ aryl; or $C_6$–$C_{10}$ aryl unsubstituted or substituted with at least one substituent selected from $C_1$–$C_8$ alkyl, $C_1$–$C_8$ alkoxy, $C_6$–$C_{10}$ aryl, nitro and halogen; said heteroaryl being a member selected from pyridyl, pyrimidinyl, thienyl, imidazolyl, thiazolyl and oxazolyl; and X is halogen.

2. The thiourea compound according to claim 1, wherein $R^1$ is a 3-trifluoromethylphenyl group.

3. The thiourea compound according to claim 1, wherein X is a chlorine atom.

4. The thiourea compound according to claim 3, wherein $R^2$, $R^3$, $R^4$ and $R^5$ are hydrogen.

5. A compound of the formula:

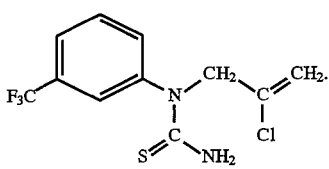

* * * * *